US008674328B2

(12) United States Patent
Fourkas et al.

(10) Patent No.: US 8,674,328 B2
(45) Date of Patent: Mar. 18, 2014

(54) REMOTE NANOSCALE PHOTOCHEMISTRY USING GUIDED EMISSION IN NANOWIRES

(75) Inventors: John T. Fourkas, Bethesda, MD (US); Linjie Li, Breinigsville, PA (US); Sanghee Nah, Laurel, MD (US)

(73) Assignee: University of Maryland College Park, College Park, MD (US)

( * ) Notice: Subject to any disclaimer, the term of this patent is extended or adjusted under 35 U.S.C. 154(b) by 225 days.

(21) Appl. No.: 13/295,800

(22) Filed: Nov. 14, 2011

(65) Prior Publication Data

US 2012/0119117 A1 May 17, 2012

Related U.S. Application Data

(60) Provisional application No. 61/413,022, filed on Nov. 12, 2010.

(51) Int. Cl.
*H05G 2/00* (2006.01)
(52) U.S. Cl.
USPC ....... 250/504 R; 977/932; 977/949; 977/950; 977/951
(58) Field of Classification Search
USPC .................. 250/504 R; 977/932, 949–951
See application file for complete search history.

(56) References Cited

U.S. PATENT DOCUMENTS

2010/0258784 A1* 10/2010 Lukin et al. ............... 257/10

OTHER PUBLICATIONS

Akimov, A. V. et al., "*Generation of Single Optical Plasmons in Metallic Nanowires Coupled to Quantum Dots*," Nature, 450:402-406 (2007).

Baldacchini, T. et al., "*Acrylic-Based Resin with Favorable Properties for Three-Dimensional Two-Photon Polymerization*," J. Appl. Phys., 95:6072-6076 (2004).
Curto, A. G. et al., "*Unidirectional Emission of a Quantum Dot Coupled to a Nanoantenna*," Science, 329:930-933 (2010).
Dickson, R. M. & Lyon, L. A., "*Unidirectional Plasmon Propagation in Metallic Nanowires*," J. Phys. Chem. B, 104:6095-6098 (2000).
Ditlbacher, H. et al., "*Silver Nanowires as Surface Plasmon Resonators*," Phys. Rev. Lett., 95:257403 (2005).
Engheta, N., "*Circuits with Light at Nanoscales: Optical Nanocircuits Inspired by Metamaterials*," Science, 317:1698-1702 (2007).
Fang, Y. et al., "*Remote-Excitation Surface-Enhanced Raman Scattering Using Propagating Ag Nanowire Plasmons*," Nano. Lett. 9:2049-2053 (2009).
Fang, Y. R. et al., "*Branched Silver Nanowires as Controllable Plasmon Routers*," Nano. Lett., 10: 1950-1954 (2010).
Farrer, R. A. et al., "*Highly Efficient Multiphoton-Absorption-Induced Luminescence from Gold Nanoparticles*," Nano. Lett., 5:1139-1142 (2005).

(Continued)

*Primary Examiner* — Michael Maskell
(74) *Attorney, Agent, or Firm* — William C. Schrot; AuerbachSchrot LLC

(57) ABSTRACT

A method of fabricating a nanodevice includes providing a nanowire having a first portion and a second portion. The nanowire has a polymer coating. A nanostructure is provided that is proximate to the second portion of the nanowire. Solely the first portion of the nanowire is irradiated with near-infrared radiation, thereby exciting the first portion to generate ultraviolet radiation. The generated ultraviolet radiation is guided from the first portion along the nanowire toward the second portion, so that a region of the polymer coating on the second portion is polymerized and bonds the nanostructure to the nanowire.

14 Claims, 15 Drawing Sheets
(2 of 15 Drawing Sheet(s) Filed in Color)

(56) References Cited

OTHER PUBLICATIONS

Han, Y. et al., "*Nonlinear Refraction of Silver Nanowires from Nanosecond to Femtosecond Laser Excitation*," Appl. Phys. B: Lasers and Optics, 94:233-237 (2009).

Hutchison, J. A. et al., "*Subdiffraction Limited, Remote Excitation of Surface Enhanced Raman Scattering*," Nano. Lett., 9:995-1001 (2009).

Kik, P.G. et al. "*Surface Plasmon Nanophotonics*," Springer (2007) pp. 1-9.

Knight, M. W. et al., "*Nanoparticle-Mediated Coupling of Light into a Nanowire*," Nano. Lett., 7:2346-2350 (2007).

Kojima, K. et al., "*A Novel Water-Soluble Photoinitiator for the Acrylic Photopolymerization Type Resist System*," Chem. Mater., 10:3429-3433 (1998).

LaFratta, C. N. et al., "*Multiphoton Fabrication*," Angewandte Chemie (Int. Ed.) 46(33):6238-6258 (2007).

Maruo, S. et al., "*Recent Progress in Multiphoton Fabrication*," Laser Photonics Rev. 2:100-111 (2008).

Muhlschlegel, P. et al., "*Resonant Optical Antennas*," Science, 308:1607-1609 (2005).

Nah, S. et al., "*Metal-Enhanced Multiphoton Absorption Polymerization with Gold Nanowires*," J. Phys. Chem. C 114:7774-7779 (2010).

Nelayah, J. et al., "*Direct Imaging of Surface Plasmon Resonances on Single Triangular Silver Nanoprisms at Optical Wavelength using Low-Loss EFTEM Imaging*," Opt. Lett., 34:1003-1005 (2009).

Pyayt, A. L. et al., "*Integration of Photonic and Silver Nanowire Plasmonic Waveguides*," Nature Nanotech., 3:660-665 (2008).

Ropp, C. et al., "*Manipulating Quantum Dots to Nanometer Precision by Control of Flow*," Nano. Lett., 10:2525-2530 (2010).

Ropp, C. et al., "*Positioning and Immobilization of Individual Quantum Dots with Nanoscale Precision*," Nano. Lett., 10:4673-4679 (2010).

Rumi, M. et al., "*Two-Photon Absorbing Materials and Two-Photon-induced Chemistry*," Photoresponsive Polymers I, Springer, vol. 213 (2008).

Sanders, A. W. et al., "*Observation of Plasmon Propagation, Redirection, and Fan-Out in Silver Nanowires*," Nano. Lett., 6:1822-1826 (2006).

Schuller, J. A. et al., "*Plasmonics for Extreme Light Concentration and Manipulation*," Nature Mater, 9:193-204 (2010).

Sun, Y. G. et al., "*Uniform Silver Nanowires Synthesis by reducing $AgNO_3$ with Ethylene Glycol in the Presence of Seeds and Poly(vinyl pyrrolidone)*," Chem. Mater., 14:4736-4745 (2002).

Sun, Y. "*Silver Nanowires—Unique Templates for Functional Nanostructures*," Nanoscale 2:1626-1642 (2010).

Sundaramurthy, A. et al., "*Toward Nanometer-Scale Optical Photolithography: Utilizing the Near-Field of Bowtie Optical Nanoantennas*," Nano. Lett., 6:355-360 (2006).

Takahara, J. et al., "*Guiding of a One-Dimensional Optical Beam with Nanometer Diameter*," Opt. Lett., 22:475-477 (1997).

Tao, A. R. et al., "*Polarized Surface-Enhanced Raman Spectroscopy on Coupled Metallic Nanowires*," J. Phys. Chem. B, 109:15687-15690 (2005).

Wang, H. et al., "*Nucleic Acid Conjugated Nanomaterials for Enhanced Molecular Recognition*," ACS Nano 3(9):2451-2460 (2009).

Yan, R. et al., "*Direct photonic-plasmonic coupling and routing in single nanowires*," Proc. Nat. Acad. Sci. USA, 106:21045-21050 (2009).

\* cited by examiner

REMOTE NANOSCALE PHOTOCHEMISTRY USING GUIDED EMISSION IN NANOWIRES

CROSS-REFERENCE TO RELATED APPLICATIONS

This application is based on U.S. Patent Application Ser. No. 61/413,022, filed Nov. 12, 2010, entitled "Nanolithography with Nanowire Arrays," which application is incorporated herein by reference in its entirety and to which priority is claimed.

STATEMENT REGARDING FEDERALLY SPONSORED RESEARCH OR DEVELOPMENT

This work was supported by the Defense Advanced Research Projects Agency as provided for by the terms of W911NF1010310. The U.S. Government has a paid-up license in this invention and the right in limited circumstances to require the patent owner to license others on reasonable terms as provided for by the terms of DMR 05-20471 awarded by The National Science Foundation.

FIELD OF THE INVENTION

The present invention relates to methods of driving localized, nanoscale photochemistry at locations remote from the point of optical excitation by guiding radiation in nanowires, and nanostructures and applications employing such methods.

BACKGROUND OF THE INVENTION

The ability of noble-metal nanowires to guide propagating surface plasmon polariton (SPP) modes with wavelengths that are considerably shorter than the corresponding free-space wavelength (e.g., see Sanders, A. W. et al., "*Observation of Plasmon Propagation, Redirection, and Fan-Out in Silver Nanowires*," Nano. Lett., 6:1822-1826 (2006); Nelayah, J. et al., "*Direct Imaging of Surface Plasmon Resonances on Single Triangular Silver Nanoprisms at Optical Wavelength using Low-Loss EFTEM Imaging*," Opt. Lett., 34:1003-1005 (2009); Ditlbacher, H. et al., "*Silver Nanowires as Surface Plasmon Resonators*," Phys. Rev. Lett., 95:257403 (2005); Dickson, R. M. & Lyon, L. A., "*Unidirectional Plasmon Propagation in Metallic Nanowires*," J. Phys. Chem. B, 104:6095-6098 (2000); Takahara, J. et al., "*Guiding of a One-Dimensional Optical Beam with Nanometer Diameter*," Opt. Lett., 22:475-477 (1997)) has driven considerable interest in SPP-based applications in areas such as light harvesting, nanoscale imaging, and spectroscopy (see Brongersma, M. L. & Kik, P. G., "*Surface Plasmon Nanophotonics*," Springer (2007); Shalaev, V. M. & Kawata, S., "*Nanophotonics with Surface Plasmons*," Elsevier (2007); Maier, S. A., "*Plasmonics: Fundamentals and Applications*," Springer (2007); Engheta, N., "*Circuits with Light at Nanoscales: Optical Nanocircuits Inspired by Metamaterials*," Science, 317:1698-1702 (2007); Fang, Y. et al., "*Remote-Excitation Surface-Enhanced Raman Scattering Using Propagating Ag Nanowire Plasmons*," Nano. Lett., 9:2049-2053 (2009); Hutchison, J. A. et al., "*Subdiffraction Limited, Remote Excitation of Surface Enhanced Raman Scattering*," Nano. Lett., 9:995-1001 (2009). However, most of these applications require the ability to combine noble-metal nanowires with other nanostructures.

On-demand fabrication of nanowire-based devices that incorporate plasmonic elements and other nanomaterials, such as quantum dots or dielectric nanoparticles, remains a challenging problem. Strategies for creating such devices have generally relied on random assembly (Knight, M. W. et al., "*Nanoparticle-Mediated Coupling of Light into a Nanowire*," Nano. Lett., 7:2346-2350 (2007); Akimov, A. V. et al., "*Generation of Single Optical Plasmons in Metallic Nanowires Coupled to Quantum Dots*," Nature, 450:402-406 (2007)) or self-assembly (Curto, A. G. et al., "*Unidirectional Emission of a Quantum Dot Coupled to a Nanoantenna*," Science, 329:930-933 (2010)), followed by searching for individual structures with the desired components and configuration. Thus, the ability to more easily assemble preselected nanostructures at predetermined locations on a metal nanowire would be beneficial for the creation of a broad range of devices.

Another issue that arises in nanophotonic devices that involve noble-metal nanowires is the inherent difficulty of coupling light into SPP modes from the far field when using conventional techniques. Momentum-matching constraints only allow efficient far-field coupling for light that is nearly parallel to the nanowire axis, a condition that is often difficult to achieve using conventional techniques, particularly over a broad range of wavelengths. This difficulty has led to the development of approaches for near-field coupling into nanowires (e.g., see Yan, R. et al., "*Direct photonic-plasmonic coupling and routing in single nanowires*," Proc. Nat. Acad. Sci. USA, 106:21045-21050 (2009), but such approaches generally rely on random assembly.

SUMMARY OF THE INVENTION

The present invention is directed to methods of guiding radiation in a nanowire. In one embodiment, a nanowire having a first portion and a second portion is provided. Solely the first portion of the nanowire is irradiated with near-infrared radiation, thereby exciting the first portion to generate ultraviolet radiation. The generated ultraviolet radiation is guided from the first portion along the nanowire toward the second portion so that the guided ultraviolet radiation is emitted from the second portion at a location remote from the first portion.

In one embodiment, a nanowire having a polymer coating is provided. The polymer coating is polymerized by the emitted ultraviolet radiation to form a polymerized region extending outwardly from the second portion of the nanowire.

In one embodiment, the nanowire is formed from a noble metal, and in particular, silver. In other embodiments, the nanowire is formed from another metal, composition or alloy, wherein the nanowire comprises a metal selected from the group consisting of silver, nickel, palladium, platinum, copper, zinc, and cadmium.

In one implementation, the emitted ultraviolet radiation is utilized to illuminate a structure for a nanoimaging application. In another implementation, the emitted ultraviolet radiation is utilized to polymerize a photoresist coating on a surface.

In one embodiment, the disclosed method further includes the step of positioning a nanoparticle at a selected position on the nanowire prior to the irradiating step. The nanoparticle is then immobilized at the selected position following irradiation. The nanoparticle may be a quantum dot, a dye-infused nanobead, or a biomolecule. In some embodiments, two or more nanoparticles are positioned and immobilized at selected positions on the nanowire. Electroosmotic flow control may be used to position the nanoparticle(s) at the selected position(s).

The present invention is also directed to a method of fabricating a nanodevice. A nanowire including a first portion and a second portion and having a polymer coating is provided. A nanostructure proximate to the second portion of the nanowire is provided. Solely the first portion of the nanowire, and not the second portion, is irradiated with near-infrared radiation, thereby exciting the first portion to generate ultraviolet radiation. The generated ultraviolet radiation is guided from the first portion along the nanowire toward the second portion so that a region of the polymer coating on the second portion is polymerized and bonds the nanostructure to the nanowire.

In one embodiment, the region of the polymer coating that is polymerized and bonded to the nanostructure is intermediate opposing ends of the nanowire. In one implementation, the bonded nanowire and nanostructure collectively have a T-shaped configuration.

In one embodiment, the method of fabricating also includes the step of positioning a nanoparticle at a selected position on the nanowire prior to the irradiating step. The nanoparticle is then immobilized at the selected position following the irradiating step. The nanoparticle may be a quantum dot, a dye-infused nanobead, or a biomolecule.

The present invention is also directed to a nanodevice including a first nanowire, a second nanowire, and a polymerized junction region extending between and interconnecting the first nanowire and the second nanowire.

In one embodiment, the first nanowire includes first and second opposing ends and a central portion, and the second nanowire includes first and second opposing ends and a central portion. In one implementation, the polymerized junction region extends between and interconnects the central portion of the first nanowire and the first end of the second nanowire so that the nanodevice has a generally T-shaped configuration.

In one embodiment, each of the first and second nanowires of the nanodevice comprises a metal selected from the group consisting of silver, nickel, palladium, platinum, copper, zinc, and cadmium.

In one embodiment, the nanodevice includes at least one nanoparticle immobilized on at least one of the first and second nanowires. The immobilized nanoparticle may be a metal nanoparticle, a quantum dot, a dye-infused nanobead, a virus, or a biomolecule.

In one embodiment, the first nanowire includes first and second opposing ends and a central portion. In one implementation, the central portion of the first nanowire has a first diameter, and the polymerized junction region has a second diameter less than the first diameter. In another implementation, the central portion of the first nanowire has a first diameter, and the polymerized junction region has a second diameter equal to or greater than the first diameter.

BRIEF DESCRIPTION OF THE DRAWINGS

The file of this patent contains at least one drawing/photograph executed in color and that copies of this patent with color drawing(s)/photograph(s) will be provided by the Office upon request and payment of the necessary fee.

As shown in FIG. 3a, metal nanowires are created electrochemically in a template. A photoresist is then selectively patterned over the nanowires, as shown in FIG. 3b. The unprotected nanowires are etched away, as shown in FIG. 3c. The photoresist is removed, leaving a nanowire array with the selected pattern, as shown in FIG. 3d.

In FIG. 5a, the light was polarized approximately parallel to the wire. Emission from the same region using radially polarized and azimuthally polarized excitation is shown in FIGS. 5b and 5c, respectively.

FIG. 8a is an optical image of AgNWs in a photoresist and FIG. 8b is an image of the same nanowires when the top of left-hand AgNW is excited with ultrafast, 730-nm pulses. FIG. 8c is a subtraction of image 8a from 8b. FIG. 8d is an SEM of the nanowires after development of the photoresist. FIG. 8e is an exploded view of the excited nanowire and the end of an adjacent nanowire. FIG. 8f is an exploded view of the distal end of the excited nanowire.

FIG. 9b is an exploded view of the contact or junction region of the two AgNWs. A thin layer of exposed photoresist is visible at the intersection or junction region of the wires. FIG. 9c illustrates a finite-difference time-domain (FDTD) simulation of the propagation of the axially-polarized electric field component generated by axially-polarized excitation in a system of crossed AgNWs. The optical field on the surface of the wire that was not irradiated indicates that there is leakage at the junction, which leads to local photopolymerization.

FIG. 10a is an SEM of an AgNW that was irradiated at one end with pulses of 800-nm light while a suspension of DINs was flowed over it. A DIN immobilized on the AgNW is circled in the inset. FIG. 10b is an SEM of an AgNW that was not irradiated while a suspension of DINs was flowed over it, whereby no DINs were immobilized on the nanowire. FIG. 10c is a series of luminescence images, at times $t_1$ to $t_4$, of a QD that was immobilized to an AgNW using GMAIL. The correlation between the blinking of the QD and the ends of the AgNW indicates that there is strong optical coupling between the two structures.

FIG. 11a illustrates a number of QDs that are visible in the EOFC microfluidic system. The control algorithm was used to position the QD nearest the AgNW in this image. Two other QDs are circled for reference. Referring to FIG. 11b, the selected QD is brought into optical contact with the AgNW using EOFC. Note that the other two QDs have also moved during this process. As shown in FIG. 11c, the selected QD is immobilized on the AgNW using GMAIL. Referring to FIG. 11d, the flow in the microfluidic channel is increased to demonstrate immobilization. While the immobilized QD remains on the AgNW, the other QDs have moved many micrometers away from their previous positions.

Referring to FIG. 12a, the upper QD is in a luminescent state and can be seen to be optically coupled to the AgNW, while the lower QD is in a dark state at this time. Referring to FIG. 12b, the lower QD is in a luminescent state and can be seen to be optically coupled to the AgNW, while the upper QD is in a dark state at this time. As shown in FIG. 12c, both QDs were in a luminescent state when this image was obtained.

DETAILED DESCRIPTION OF THE INVENTION

Figure 1:
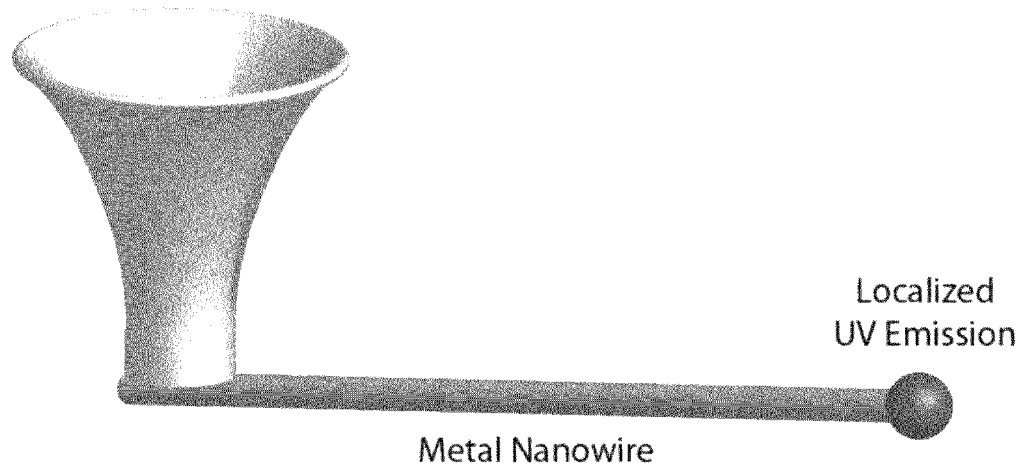
FIG. 1 illustrates a metal nanowire, wherein one end of the nanowire is being irradiated with short-pulsed, near-infrared light, which generates visible and UV light that is then guided along the nanowire and emitted from the opposite end of the nanowire. Thus, light at the shortest wavelengths along with the generated visible and UV radiation is wave-guided by the nanowire and emitted at the opposite end where it can be used, for example, to drive photochemistry or photophysics applications.

The present invention is directed to noble-metal nanostructures that act as waveguides for surface plasmon polaritons (SPPs). In particular, the invention relates to nanowires, especially silver nanowires (AgNWs), that are utilized to drive localized, nanoscale photochemistry at locations many micrometers away from the point of optical excitation and without affecting the surrounding medium. The excitation of one end of an AgNW by ultrafast, near-infrared (near-IR) radiation generates broadband luminescence that is guided along the AgNW to the opposite end thereof, which drives localized photochemistry at the opposite end of the nanowire. If another nanostructure is in contact with the nanowire, leakage of light from the nanowire waveguide may also drive localized photochemistry at such point of contact of the other nanostructure. The generation and guiding of broadband radiation in nanowires to perform remote photochemistry has many potential applications in areas such as nanolithography, nanofabrication, and nanoimaging.

As used herein, the term "nanowire" denotes a substantially cylindrical, polygonal composition, being either solid or hollow, and having a diameter or cross-section of between about 5 nanometers (nm) and about 50 nm, more preferably, between about 10 nm and about 50 nm, and more preferably still between about 10 nm and about 40 nm. Most preferably, such nanowires will have an axial length of between about 20 nm and about 200 nm, more preferably, between about 30 and about 200 nm, and more preferably still between about 40 nm and about 200 nm. Most preferably, such nanowires will have an aspect ratio (i.e., the ratio of the width of the nanowire to its length) between about 2:5 and 4:5, between about 1:2 and 7:10, or about 3:5.

The term "nanoparticle," including a metal nanoparticle, denotes a particle having a diameter or cross-section of between about 1 nm and about 100 nm. The term "biomolecule" refers to any molecule that is produced by a living organism, such as proteins, polysaccharides, lipids, nucleic acids, and small molecules such as metabolites. Quantum dots refer to nanostructures having a diameter or cross-section of about 2 nm or greater. Nanobeads refer to nanostructures having a diameter of about 10 nm or greater.

Although the present invention is exemplified with regard to silver nanowires, it will be understood that nanowires formed of other metals, such as nickel, palladium, platinum, copper, zinc or cadmium, may be utilized. The nanowires of the invention may comprise a single metal or may be an alloy (i.e., a solution mixture) or a composite (i.e., non-solution mixture) comprising one, two, three or more additional metals (see, Sun, Y. "*Silver Nanowires—Unique Templates For Functional Nanostructures*," Nanoscale 2:1626-1642; Wang, H. et al., "*Nucleic Acid Conjugated Nanomaterials for Enhanced Molecular Recognition*," ACS Nano 3(9):2451-2460 (2009)). Moreover, any of a variety of methods known in the art may be used to form the metal nanowires used in the present invention.

Most work on the plasmonic properties of metal nanowires has focused on their linear optical behavior. However, the nonlinear optical (NLO) properties of nanowires are beginning to attract interest. Han, Y. et al., "*Nonlinear Refraction of Silver Nanowires from Nanosecond to Femtosecond Laser Excitation*," Appl. Phys. B: Lasers and Optics, 94:233-237 (2009); Schuller, J. A. et al., "*Plasmonics for Extreme Light Concentration and Manipulation*," Nature Mater, 9:193-204 (2010); Nah, S. et al., "*Metal-Enhanced Multiphoton Absorption Polymerization with Gold Nanowires*," J. Phys. Chem. C," 114:7774-7779 (2010).

We have previously demonstrated the connection between two NLO effects, multiphoton-absorption-induced luminescence (MAIL) and metal-enhanced multiphoton absorption polymerization (MEMAP), in gold nanowires. Multiphoton absorption polymerization ("MAP") is based on the absorption of two or more photons of light to excite photoinitiator molecules that drive polymerization in a pre-polymer resin (LaFratta, C. N. et al., "*Multiphoton Fabrication*," Angewandte Chemie (Int. Ed.) 46(33):6238-6258 (2007); Maruo, S. et al., "*Recent Progress in Multiphoton Fabrication*," Laser Photonics Rev. 2:100-111 (2008); Rumi, M. et al., "*Two-Photon Absorbing Materials and Two-Photon-induced Chemistry*," Photoresponsive Polymers I, Springer, Vol. 213 (2008)).

In MAIL, the irradiation of one end of a nanowire, an in particular a nanowire made of a noble metal (e.g., an AgNW) with short-pulsed, near-IR radiation, generates light by excitation of the nanowire that spans the visible spectrum into the ultraviolet (UV). Field enhancement by a nanowire can lead to the efficient multiphoton absorption of ultrafast pulses of near-IR light, producing broadband visible luminescence. Farrer, R. A. et al., "*Highly Efficient Multiphoton-Absorption-Induced Luminescence from Gold Nanoparticles*," Nano. Lett., 5:1139-1142 (2005). The "lightning-rod" effect (see Muhlschlegel, P. et al., "*Resonant Optical Antennas*," Science, 308:1607-1609 (2005); Tao, A. R. et al., "*Polarized Surface-Enhanced Raman Spectroscopy on Coupled Metallic*

Nanowires," J. Phys. Chem. B, 109:15687-15690 (2005)) makes excitation especially efficient at the ends of nanowires.

In MEMAP, a noble-metal nanostructure enhances the efficiency of multiphoton exposure of a negative-tone photoresist. See Sundaramurthy, A. et al., "*Toward Nanometer-Scale Optical Photolithography: Utilizing the Near-Field of Bowtie Optical Nanoantennas,*" Nano. Lett., 6:355-360 (2006). Polymeric features can be created at the ends of a nanowire at a laser fluence (integrated exposure) considerably lower than that needed in the bulk photoresist. MEMAP occurs because efficient generation of MAIL leads to single-photon exposure of the photoresist in close proximity to the region of the nanostructure that luminesces. See Nah, S. et al., "*Metal-Enhanced Multiphoton Absorption Polymerization with Gold Nanowires,*" J. Phys. Chem. C 114:7774-7779 (2010).

Referring to FIG. 1, in a medium with appropriate dielectric properties, the nanowire acts as a waveguide for the radiation with short wavelengths at an end of the nanowire, whereby emitted light is guided along and travels down the nanowire from the irradiated end to an opposite end where it is emitted as a localized visible and UV emission.

Figure 2:
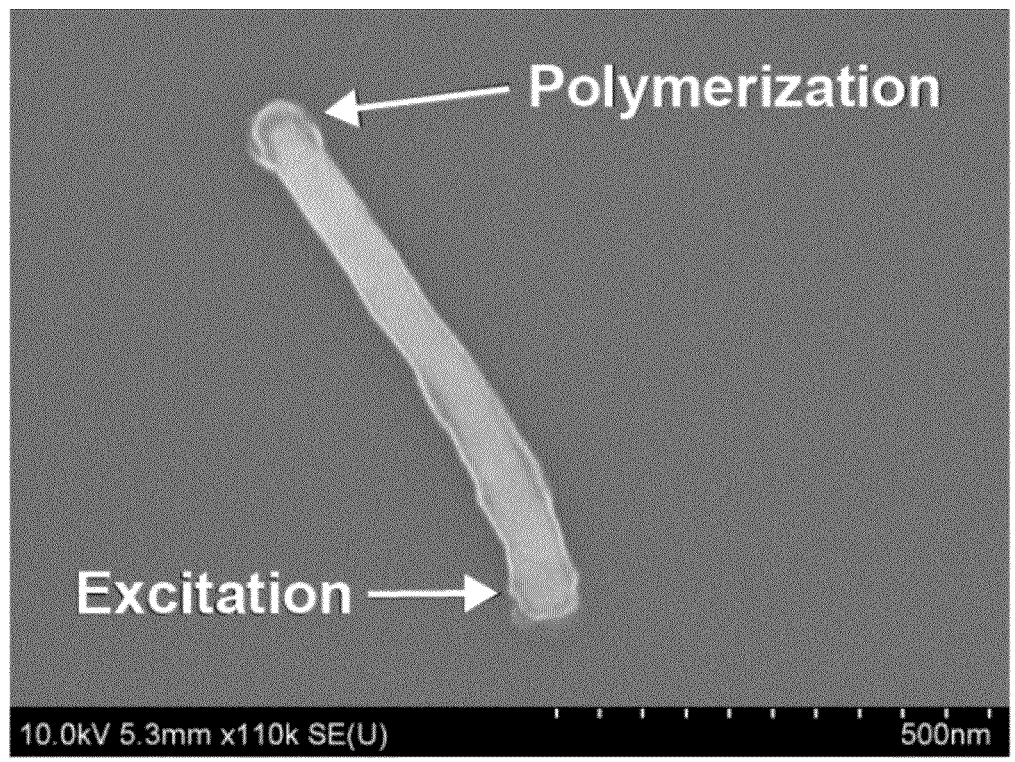
FIG. 2 is an image of a single nanowire, demonstrating excitation of one end of the nanowire by near-infrared light that leads to UV photopolymerization at the opposite end of the nanowire.

Referring to FIG. 2, irradiation of one end of a nanowire with near-IR radiation results in excitation of the nanowire, which in turn may lead to exposure of a photoresist at the opposite end of the nanowire with UV radiation. This exposure occurs in a region that is defined in part by the diameter of the nanowire, and results in polymerization of the photoresist. Thus, using a nanowire that is, for example, 20 nm in diameter can lead to exposure of a feature in the photoresist that is also on the order of about 20 nm or less in diameter. In some embodiments, the nanowire may include a tapered end, so that the resulting feature in and/or polymerization of the photoresist has a diameter less than the diameter of a central portion of the nanowire. In other embodiments, the nanowire may include a flanged or flared end such that the resulting feature in the photoresist has a diameter greater than the diameter of the central portion of the nanowire.

There are two possible mechanisms for broadband emission from the distal end of an irradiated nanowire. One possibility is that the emission from the excited end propagates to the distal end, where it is emitted. The other possibility is that the excitation pulse itself propagates along the nanowire and generates MAIL at the distal end. A number of lines of evidence support the first mechanism. First, because MAIL is generated within the wire, a significant portion of the emission is inherently momentum matched and should propagate efficiently to the distal end. Second, as shown by FDTD simulations, attenuation of the excitation pulse due to propagation down a nanowire should decrease the efficiency of the nonlinear excitation process to a significant extent. Third, the emission spectrum from the distal end differs from that at the excited end (see FIG. 6, discussed in further detail below). Guided luminescence would be expected to exhibit frequency-dependent attenuation in the nanowire, whereas luminescence generated at the distal end by a guided excitation pulse should have the same spectrum as the luminescence at the excited end.

Figure 3:
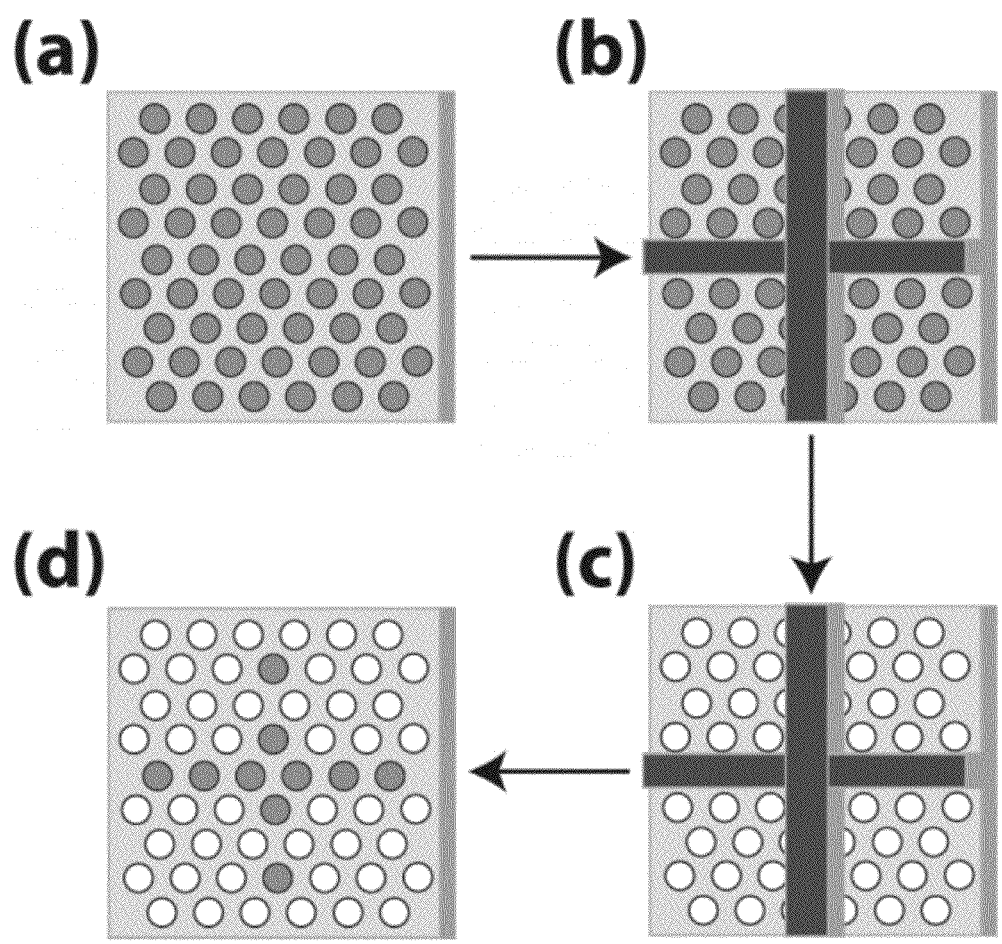
FIG. 3 illustrates the creation of an exemplary patterned set of nanowires.

The disclosed methods of nano-wire guided radiation may be utilized for various applications, including large-area nanolithography. For example, a periodic metal nanowire array may be created in a dielectric template, such as a porous aluminum oxide membrane, through electrodeposition. Referring to FIG. 3, the creation of an exemplary patterned set of nanowires is illustrated. The nanowires may be formed from silver or some other metal, and act as UV waveguides. As shown in FIG. 3a, metal nanowires are created electrochemically in a template. A photoresist is then selectively patterned over the nanowires, as shown in FIG. 3b. The unprotected nanowires are etched away, as shown in FIG. 3c. The photoresist is removed, leaving a nanowire array with the selected pattern, as shown in FIG. 3d. After the nanowire array has been fabricated, a photoresist pattern may be formed on its exterior upper surface utilizing a high-resolution technique, such as electron-beam lithography. Nanowires that are not protected by the resist may be selectively etched away. The remaining resist is then removed, leaving a selected pattern of nanowires.

Figure 4:
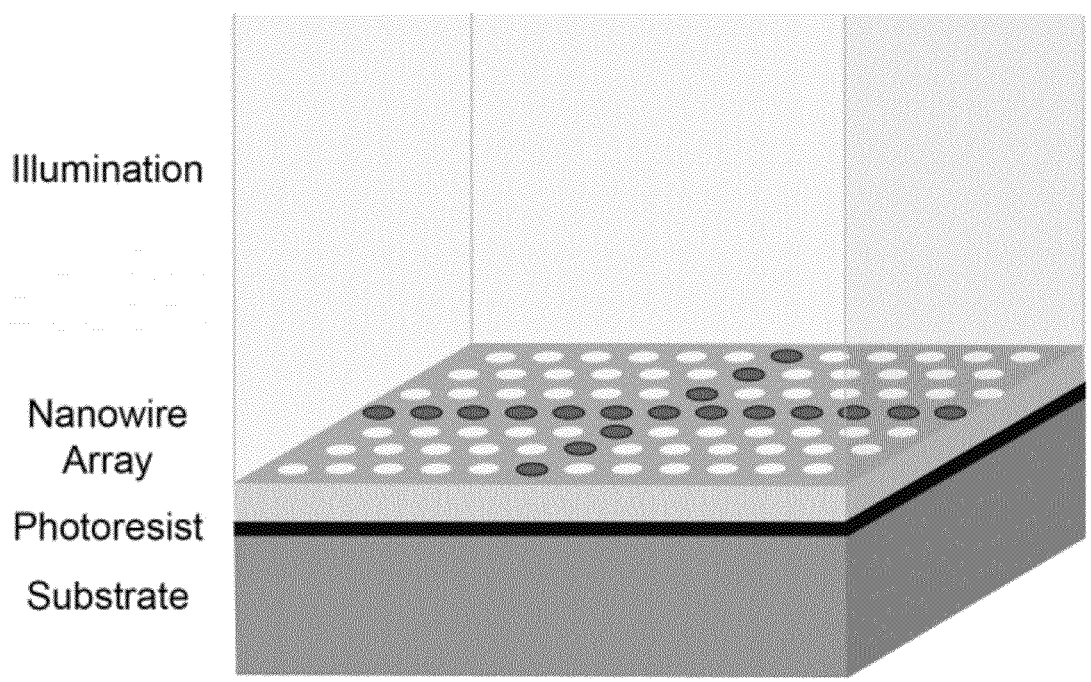
FIG. 4 illustrates an exemplary implementation of nanowire lithography according to an embodiment of the present invention.

Referring to FIG. 4, an exemplary implementation of wire lithography is illustrated. A relatively thin layer of photoresist is coated on a substrate. A major surface of the nanowire array or template is placed in contact with the photoresist so that ends of the nanowires are in contact with or proximate to the photoresist. The opposing surface of the template is irradiated with short-pulsed, near-IR radiation, so that the correspondingly positioned opposite ends of the nanowires are also exposed to near-IR light. The exposed ends of the nanowires are thereby excited and emit visible and UV radiation. This emitted visible and UV light is guided along the nanowires toward the surface of the template adjacent the photoresist coating, and delivered to the ends of the nanowires to expose the photoresist locally.

Thus, near-IR light that is delivered to one side of the template generates visible and UV light via excitation of the nanowire. The generated visible and UV radiation, along with the shorter wavelengths of the irradiating light, are transported to the opposite side of the template via the nanowires to expose the photoresist. This nanowire-guided light may be utilized in photochemistry, photophysics, or nanoimaging applications with nanoscale precision over a relatively large area. Note that the near-IR radiation does not expose the photoresist directly. As such, all exposure takes place in the near field to create nanoscale features. If desired, the template may be translated and re-exposed any number of times. The disclosed methods make possible the large-area fabrication of nanoscale features with near-IR radiation. Thus, high-vacuum conditions are not required, and beams may be steered with conventional optics, reducing fabrication costs tremendously.

Having now generally described the invention, the same will be more readily understood through reference to the following experiments and additional discussion, which are provided by way of illustration and are not intended to be limiting of the present invention unless specified.

Methods

AgNWs were synthesized using a reported procedure (Sun, Y. G. et al., "*Uniform Silver Nanowires Synthesis by reducing $AgNO_3$ with Ethylene Glycol in the Presence of Seeds and Poly(vinyl pyrrolidone),*" Chem. Mater., 14:4736-4745 (2002)). The substrates used were microscope cover slips functionalized with acrylate groups to promote polymer adhesion (Baldacchini, T. et al., "*Acrylic-Based Resin with Favorable Properties for Three-Dimensional Two-Photon Polymerization,*" J. Appl. Phys., 95:6072-6076 (2004)). The water-based acrylic photoresist was composed of 50 wt % ethoxylated-15 trimethylolpropane triacrylate (SR 9035, Sartomer), 49 wt % distilled water, and 1 wt % of sodium 4-[2-(4-morpholino)benzoyl-2-dimethylamino]butylbenzenesulfonate (MBS) (Kojima, K. et al., "*A Novel Water-Soluble Photoinitiator for the Acrylic Photopolymerization Type Resist System,*" Chem. Mater., 10:3429-3433 (1998)).

For the AgNW junction experiments, an acrylic photoresist with IRGACURE® 184 (BASF Corp.) as the initiator was used (Nah, S. et al., "*Metal-Enhanced Multiphoton Absorption Polymerization with Gold Nanowires,*" J. Phys. Chem. C, 114:7774-7779 (2010)). Additional description of the laser and microscope system used for MAIL excitation and imaging is provided in Nah, S. et al., "*Metal-Enhanced Multiphoton Absorption Polymerization with Gold Nanowires,*" J. Phys. Chem. C, 114:7774-7779 (2010), and descriptions of the EOFC system and associated photoresist are provided in Ropp, C. et al., "*Manipulating Quantum Dots to Nanometer Precision by Control of Flow,*" Nano. Lett., 10:2525-2530 (2010) and Ropp, C. et al., "*Positioning and Immobilization of Individual Quantum Dots with Nanoscale Precision,*" Nano. Lett., 10:4673-4679 (2010).

The dye-infused nanobeads (DINs) were $0.14 \times 10^{-10}$% (w/v) carboxylic acid-functionalized Fluorescent Microspheres Polystyrene (Phosphorex, Inc.) and the quantum dots (QDs) were 100 pM QTRACKER® 655 PEG CdSe/ZnS (Invitrogen Corp.). The finite-difference time-domain (FDTD) simulations were performed utilizing an FDTD simulation software package developed at MIT to model electromagnetic systems (MEEP). The dielectric functions of the materials used in the simulations were fitted to experimental data.

AgNW Guided, Non-Linearly Generated Emission

Figure 5:
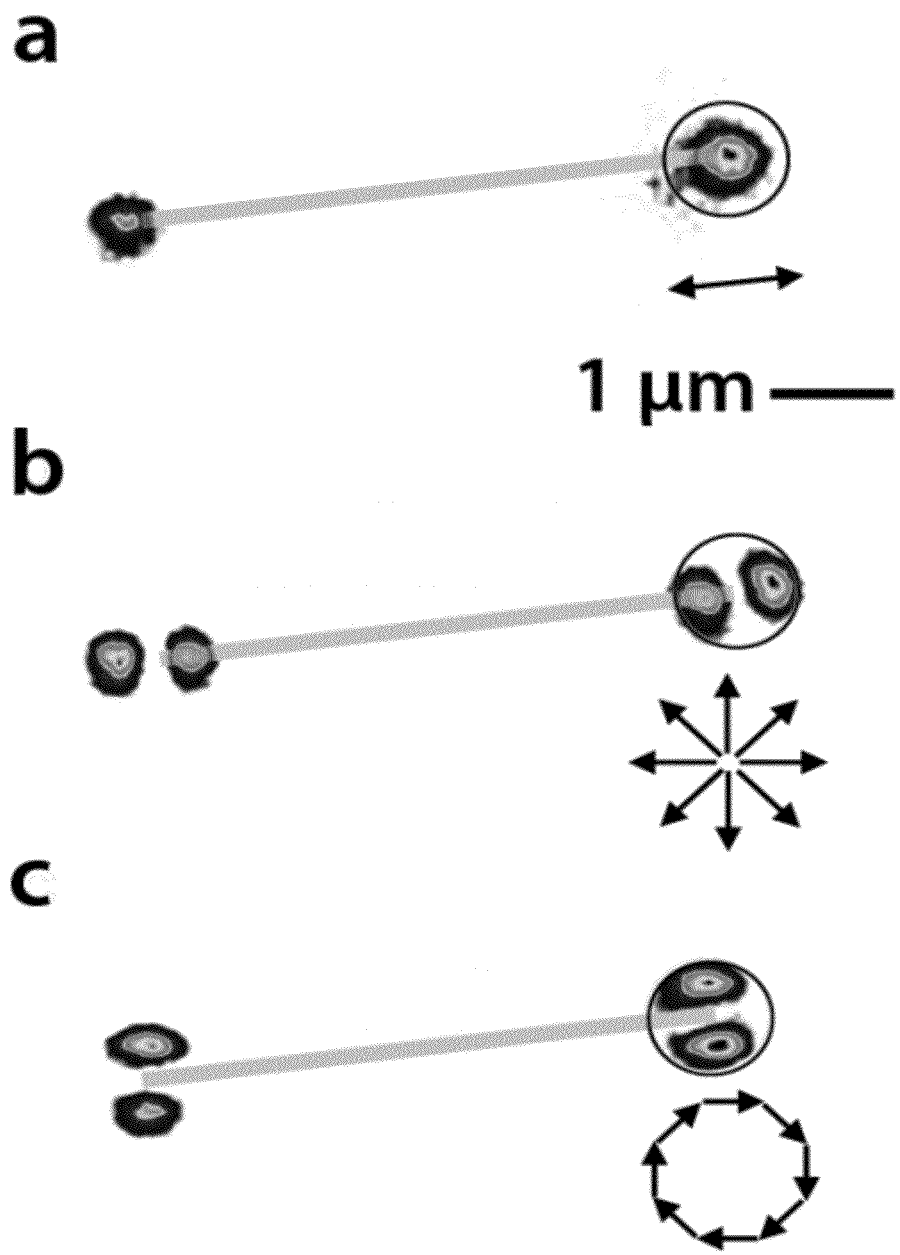
FIG. 5 illustrates AgNW emission images using pulsed 800-nm excitation with different polarizations. Emission from the region of the AgNW in the circle as a function of the position irradiated is shown in FIG. 5a. The gray rectangle indicates the approximate position of the AgNW. The color at each point in the image indicates the intensity of emission in the circle region when that point is irradiated. Red represents the highest emission intensity. The strongest signal is observed when the end of the wire that is being observed is excited, but significant emission is also observed when the far end of the AgNW is excited.

It was demonstrated that AgNWs exhibit MAIL when excited with near-infrared, ultrafast pulses. Referring to FIG. 5, the luminescence emanating from one end of an AgNW was collected by a single-photon-counting avalanche photodiode, while all other luminescence was blocked. The luminescence intensity from this region was then collected as a function of the position of the excitation beam. With linearly-polarized excitation (FIG. 5a), the most efficient emission was observed when the polarization was along the axis of the nanowire, in agreement with FDTD simulations. While the observed luminescence is brightest when the end being excited is observed, a substantial emission signal was also observed at this same position when the far end of the wire was illuminated.

Figure 6:
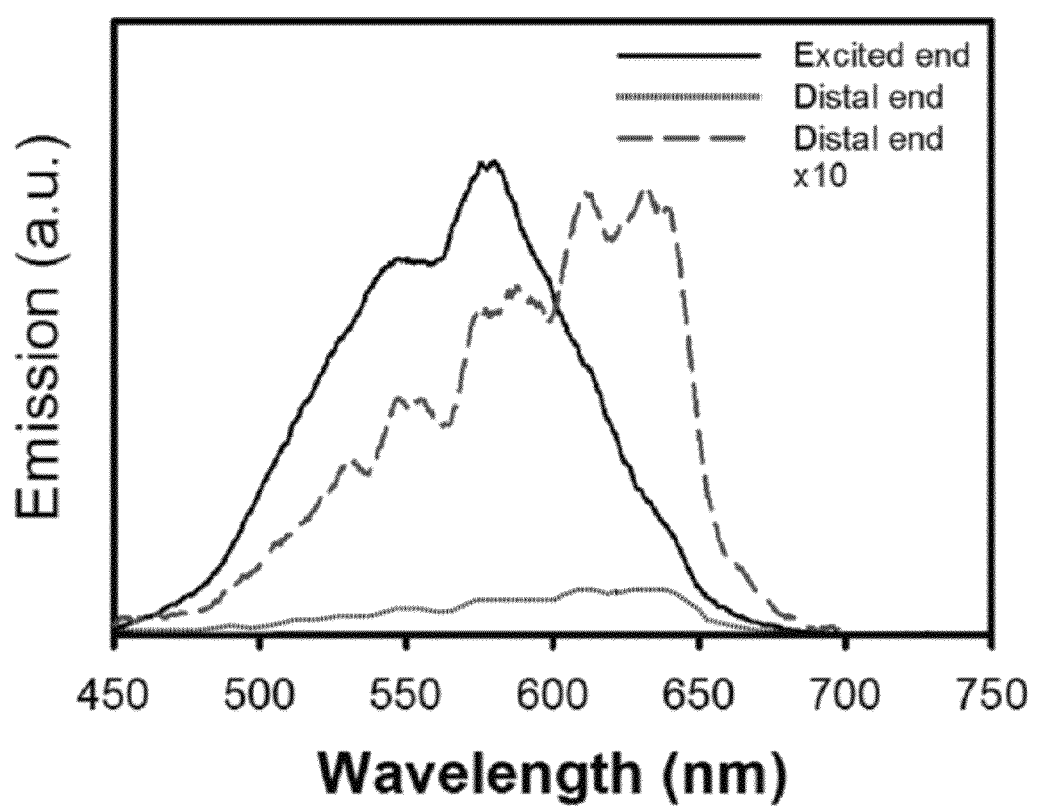
FIG. 6 is a graph illustrating representative broadband emission from the excited and distal ends of an AgNW. The long-wavelength portion of each spectrum is attenuated due to a filter that was used to block scattered excitation light.

Emission spectra collected from this region of the AgNW spanned most of the visible region of the electromagnetic spectrum, regardless of which end of the wire was excited, as shown in FIG. 6. The shape of the emission spectrum at each end of the nanowire did not depend on excitation intensity for all excitation intensities at which emission could be observed.

As an additional test that distal emission arises from guided luminescence, we generated MAIL excitation images using spatially non-uniform polarization states. The excitation image for radially polarized light is shown in FIG. 5b, and the excitation image for azimuthally polarized light is shown in FIG. 5c. In both cases, emission is observed from the distal end of the wire only when the portion of the beam that is polarized along the AgNW overlaps with the excited end of the wire. For both of these polarizations, two excitation lobes appear at each end of the AgNW, corresponding to the positions in the excitation beam in which light is polarized along the nanowire. In order for the excitation pulse to propagate along the nanowire, it must be momentum-matched, which means that the propagation vector must have a significant, positive projection along the vector leading from the excited end of the wire to the distal end. In the case of radially polarized light, only one of these lobes (appearing "within" the wire in FIG. 1b) can satisfy momentum matching for the fundamental. In the case of azimuthally polarized light, both lobes are at the sides of the wire, and so neither lobe can satisfy momentum matching.

The images shown in FIG. 5 provide strong evidence that the observed distal emission arises from guided, nonlinearly generated emission, as opposed to luminescence generated at the distal end by guided excitation pulses. GMAIL thus describes the process through which excitation of one end of an AgNW leads to distal emission. GMAIL offers the opportunity to deliver broadband, visible radiation to perform photochemistry in a nanoscale spatial region that is distant from the site of excitation. Because MAIL can be excited efficiently and selectively at the end of an AgNW, photochemistry can be localized at the ends of an AgNW without being driven in the surrounding bulk medium.

Figure 7:
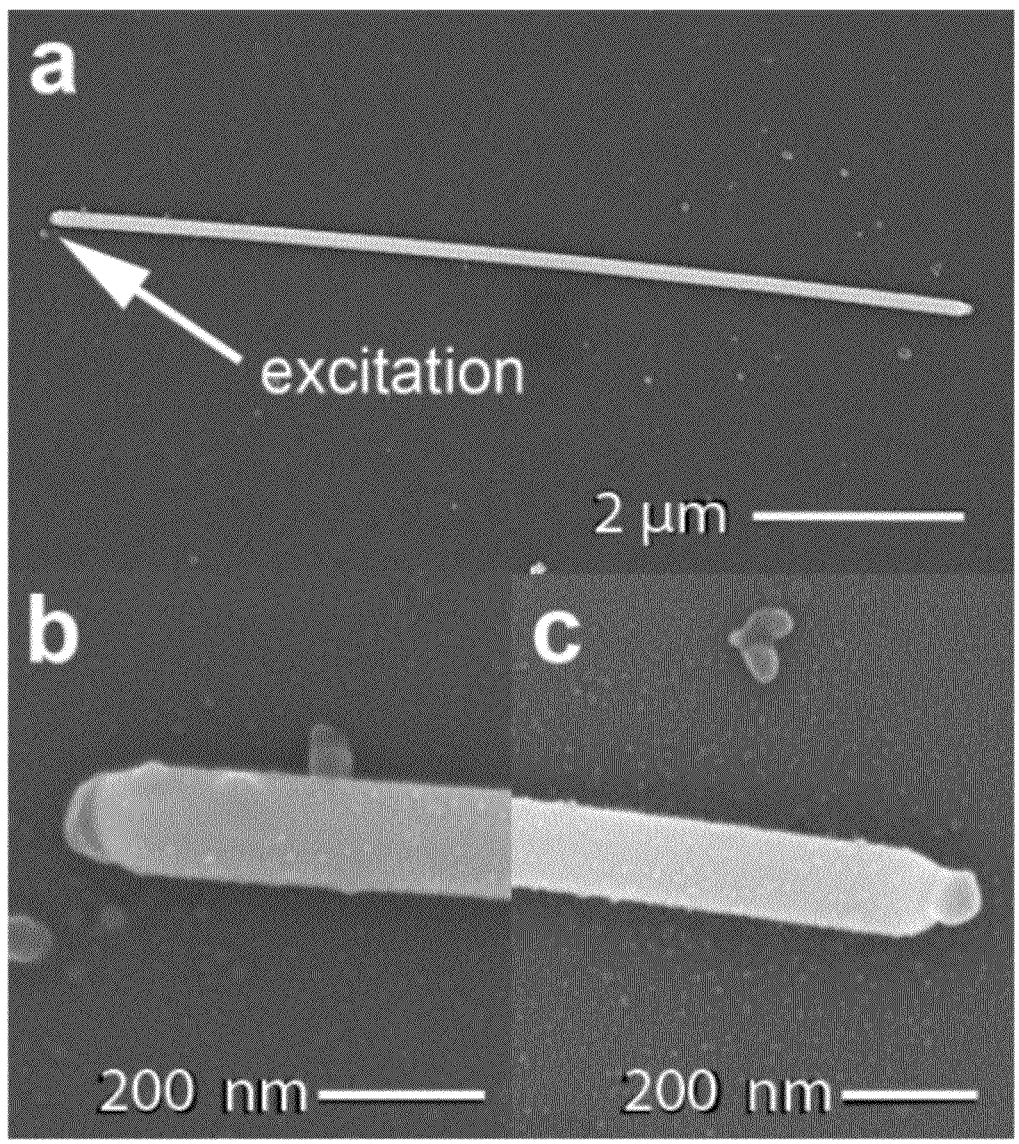
FIG. 7 are SEM images of an AgNW demonstrating remote, localized photochemistry driven by GMAIL. An SEM of an AgNW on a glass substrate is shown in FIG. 7a. The AgNW was immersed in a negative-tone photoresist, and then excited with 730-nm pulses at the location indicated in the image. An SEM of the end of the AgNW that was excited is shown in FIG. 7b. The structure at the end of the nanowire is exposed photoresist. An SEM of the opposite distal end of the AgNW is shown in FIG. 7c, which also has a polymerized region even though this end was many micrometers away from the excitation region.

The use of GMAIL to perform localized photochemistry at a distance is further illustrated in FIG. 7. Scanning electron microscopy (SEM) images of an AgNW that was immersed in a liquid, negative-tone photoresist is shown in FIG. 7a. One end of the AgNW was irradiated with 730-nm pulses at a fluence too low to expose the bulk photoresist. Exposed photoresist is observed at both ends of the AgNW, shown in FIGS. 7b and 7c. The polymerized region at the distal end (FIG. 7c) is significantly smaller than the region at the excited end (FIG. 7b), and has a diameter that is smaller than that of the AgNW, further supporting waveguiding as the source of the distal emission. Additionally, while scattering can sometimes be observed from nanowires that are near the site of excitation, polymer is not observed in the regions that exhibit such scattering.

Additional tests demonstrated the propagation of the axially-polarized electric field component of 730 nm and 400 nm light with axial polarization coupled into one end of the AgNW. Axial excitation leads to the strong propagation of the surface plasmon mode along the nanowire, resulting in strong electric field enhancement at the distal end of the nanowire (the "lightning rod" effect). The surface plasmon wavelength is shorter than the wavelength of the light outside, which is expected since the surface plasmon dispersion in Ag bends strongly downwards and away from the "light line" in the visible range. This effect leads to the decoupling of the surface plasmon modes from the outside propagating wave, enhancing the waveguiding function of the AgNW and the resulting selective resist polymerization at the distal end. Other tests demonstrated the propagation of the transverse-polarized electric field component of 400 nm light with transverse polarization coupled into one end of the AgNW, whereby excitation of the surface plasmon was suppressed for this polarization (and there was no "lightning rod" effect).

Comparison of Scattering and Waveguiding

Figure 8:
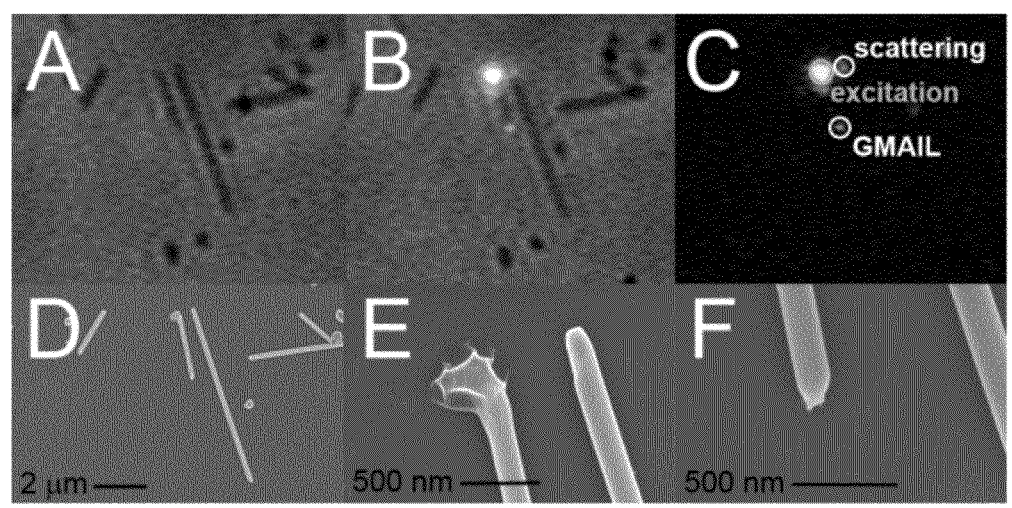
FIG. 8 illustrates a comparison of scattering and waveguiding.

When light is generated at one end of an AgNW, distal emission could occur through either plasmonic waveguiding or scattering. To test whether scattering could be responsible for the distal emission observed, we studied groups of AgNWs for which scattering is observed on nanowires near the one that is excited. An example of one such study is shown in FIG. 8. We chose two nearly parallel AgNWs, and excited the end of one that was near the end of the other (FIGS. 8a-8c). Emission was observed at the end of the excited AgNW, and scattering was observed from the end of the other nearby AgNW. The distal end of the AgNW that was excited also exhibited emission. To test whether the distal emission arose from waveguided emission or from scattering of light, these experiments were performed in a photoresist, and the AgNWs were imaged using SEM after the resist was developed. As seen in FIGS. 8d-8f, polymer is observed at both the excited end and the distal end of the first nanowire. However, the end of the neighboring nanowire shows no polymer. Thus, scattering is not sufficiently intense to cause polymerization, and thus it may be concluded that the polymer at the distal end of the excited nanowire is the result of GMAIL.

Simulations of the electromagnetic fields and the response parameters were carried out by employing FDTD simulations, implemented via MEEP. The dielectric functions of the materials (e.g. Ag) used in the simulations were fitted to the experimental data. A selective cross-checking of the simulated results was carried out by employing the Microwave Studio software from CST. Detailed calculations were performed for excitation wavelengths of 730 nm and 400 nm using both transverse and axial polarizations. Rather than have these colors generated in the AgNW, light was coupled into the end of the AgNW in the simulations. However, the results are expected to be directly relevant to light generated nonlinearly at the end of the nanowire.

Spot-Welding AgNWs

Figure 9:
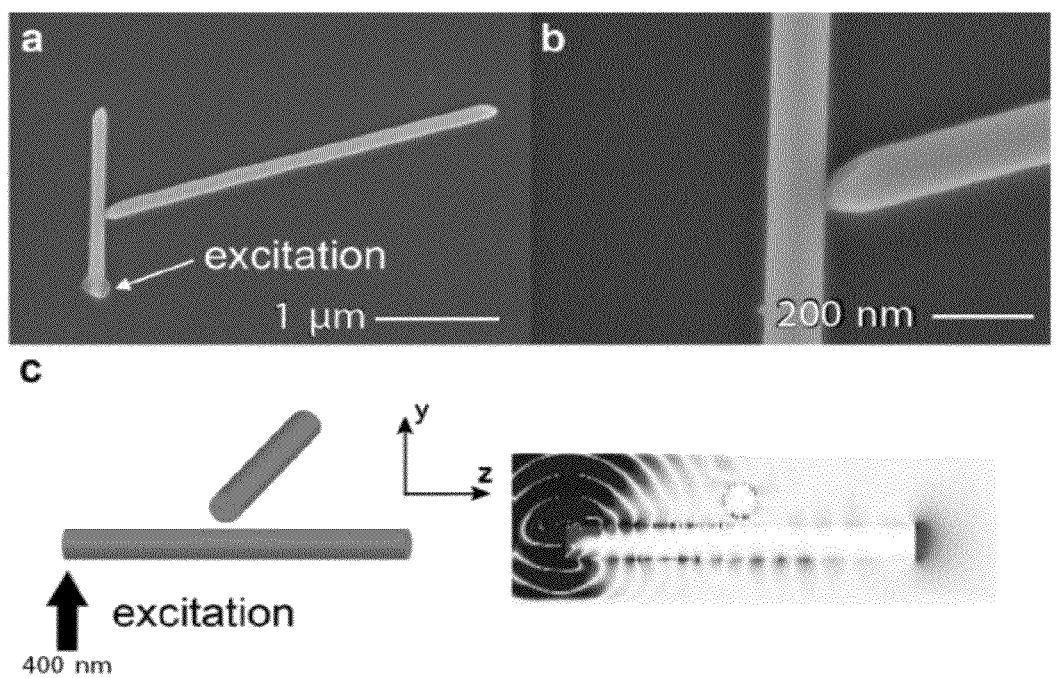
FIG. 9 includes SEM images demonstrating "spot welding" of two AgNWs using GMAIL. An SEM of two AgNWs connected or welded together in a T configuration on a glass substrate is shown in FIG. 9a. The AgNWs were immersed in a negative-tone photoresist, and the region indicated was irradiated with pulses of 800-nm light.

When another nanostructure comes into contact with an AgNW, the waveguide becomes leaky at the junction (e.g., see Sanders, A. W. et al., "*Observation of Plasmon Propagation, Redirection, and Fan-Out in Silver Nanowires*," Nano. Lett., 6:1822-1826 (2006); Fang, Y. R. et al., "*Branched Silver Nanowires as Controllable Plasmon Routers*," Nano. Lett., 10: 1950-1954 (2010)), providing an opportunity to drive localized photochemistry. To illustrate the potential of photochemistry based on waveguided luminescence, we demonstrate the precision fabrication of nanophotonic devices by "spot-welding" QDs at selected locations on AgNWs. FIG. 9a illustrates a SEM of two AgNWs connected or "welded" together in a T-shaped configuration. The individual nanowires were first immersed in an acrylic photoresist, and one end of the "crossbar" AgNW was then excited. Photoresist exposure in the junction region is visible in FIG. 9b. Thus, contact with another nanostructure can cause sufficient leakage of GMAIL to drive localized photochemistry.

While the coupling of nanowire excitation to the outside fields is suppressed in the AgNW, coupling does occur when another metallic nanostructure is placed within the near-field range, away from the AgNW surface. For example, the FDTD simulation for axial excitation at 400 nm shows that the excited nanowire waveguides the surface plasmon, still exhibiting strong "lightning rod" effect, but also couples strongly to the crossed nanowire. "hot spots" of the electric field appeared on the surface of the other AgNW, thereby causing polymerization of the resist.

Immobilization of DINs and QDs

A radiative species that is near an AgNW can cause light to couple into the nanowire's SPP modes (see Akimov, A. V. et al., "*Generation of Single Optical Plasmons in Metallic Nanowires Coupled to Quantum Dots*," Nature, 450:402-406 (2007); Curto, A. G. et al., "*Unidirectional Emission of a Quantum Dot Coupled to a Nanoantenna*," Science, 329:930-933 (2010)). This phenomenon is attractive for use in nanophotonic devices. However, nanophotonic devices that employ AgNWs are generally created via uncontrolled deposition of one or more nanoparticle emitters, leading to a low device yield (Pyayt, A. L. et al., "*Integration of Photonic and Silver Nanowire Plasmonic Waveguides*," Nature Nanotech., 3:660-665 (2008)). GMAIL provides a means for high-precision fabrication of such devices with preselected nanowires. This process begins with the immersion of a substrate with AgNWs in a liquid photoresist containing nanostructures, such as dye-infused nanobeads (DINs) or quantum dots (QDs). Nanostructures are immobilized on a selected nanowire by irradiating one of its ends Immobilization of a nanostructure occurs when sufficient optical coupling exists between the nanostructure and the AgNW, which is the condition desired for the fabrication of nanophotonic devices. A microfluidic system was used to flow a suspension of DINs over AgNWs in a water-based photoresist while the ends of selected nanowires were irradiated.

Figure 10:
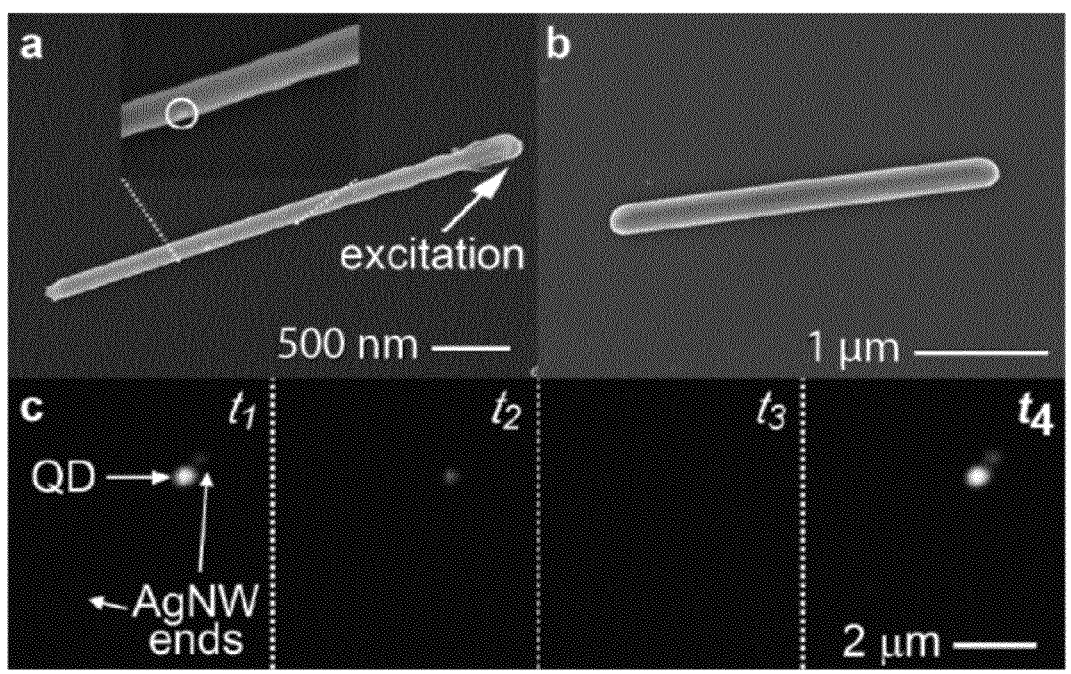
FIG. 10 includes SEM images demonstrating the immobilization of nanoparticles on AgNWs using GMAIL.

As shown in FIG. 10a, DINs were immobilized on irradiated nanowires. Control nanowires that were not irradiated had few or no attached DINs, as shown in FIG. 10b. For the fabrication of the nanophotonic device using GMAIL, electroosmotic flow control (EOFC) (see Ropp, C. et al., "*Manipulating Quantum Dots to Nanometer Precision by Control of Flow*," Nano. Left., 10:2525-2530 (2010); Ropp, C. et al., "*Positioning and Immobilization of Individual Quantum Dots with Nanoscale Precision*," Nano. Lett., 10:4673-4679 (2010)), was used to manipulate cadmium selenide (CdSe) QDs in a microfludic system containing a photoresist. An individual QD was delivered to a selected position on an AgNW. When the QD was in the desired position, the end of the AgNW was irradiated with ultrafast pulses, immobilizing the QD.

Immobilized QDs exhibit strong optical coupling to the nanowires, as can be seen from the synchronized blinking of the QD and the ends of the nanowire, shown in FIG. 10c. The immobilization of two QDs on a single nanowire was also demonstrated. FDTD simulations indicate that the fields on the surface of a QD and on a nearby AgNW that is being excited are of similar magnitude, suggesting that a polymer film a few nanometers thick forms on the AgNW, and that a similar film forms on the QD and immobilizes the QD when it is coupled optically to the AgNW.

Figure 11:
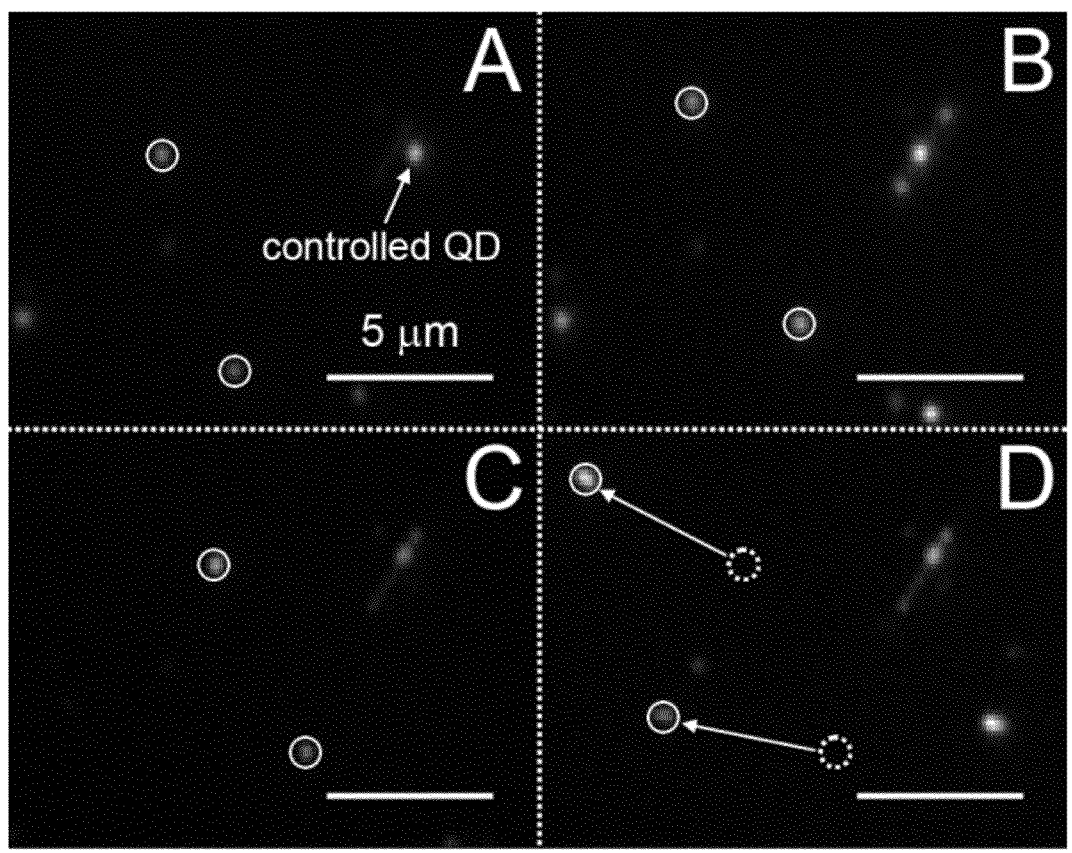
FIG. 11 illustrates the immobilization of a QD on an AgNW.

Another experiment demonstrating the immobilization of a QD on an AgNW is shown in FIG. 11. EOFC in a water-based photoresist was used for nanopositioning of individual QDs on AgNWs. Our fluid was composed of 40 vol % ethoxylated-15 trimethylolpropane triacrylate (SR-9035, Sartomer), 1.35 wt % Acrysol RM-825 rheology modifier (Rohm and Haas), 1 wt % sodium 4-[2-(4-Morpholino)benzoyl-2-dimethylamino]butylbenzenesulfonat photoinitiator, 0.3 wt % erucyl dimethyl amidopropyl betaine surfactant, and 200 pM QTracker PEG CdSe/ZnS 655 nm QDs in deionized water. The substrate was a polydimethylsiloxane surface. FIG. 11 illustrates frames from a video of the immobilization experiment. EOFC is used to bring a selected QD into proximity of an AgNW. When the QD is in optical coupling range, emission from the QD can be observed at the ends of the AgNW. One end of the AgNW is irradiated with ultrafast, 800-nm pulses with a power of about 0.75 mW at the nanowire, immobilizing the QD. Even at high flow velocities, the QD remains tethered to the AgNW.

Figure 12:
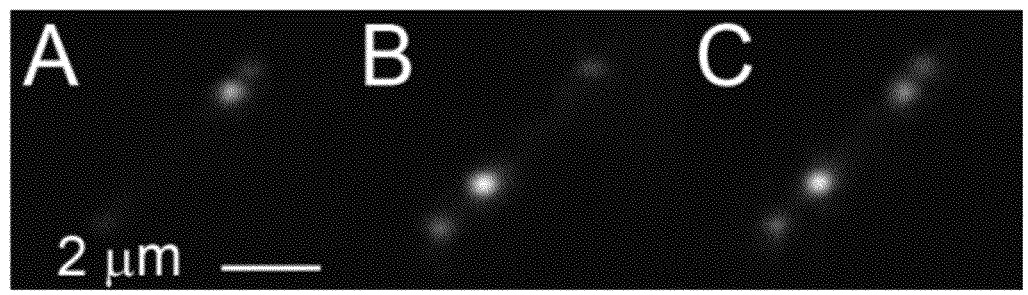
FIG. 12 illustrates the immobilization of two QDs on an AgNW.
Figure 13A:
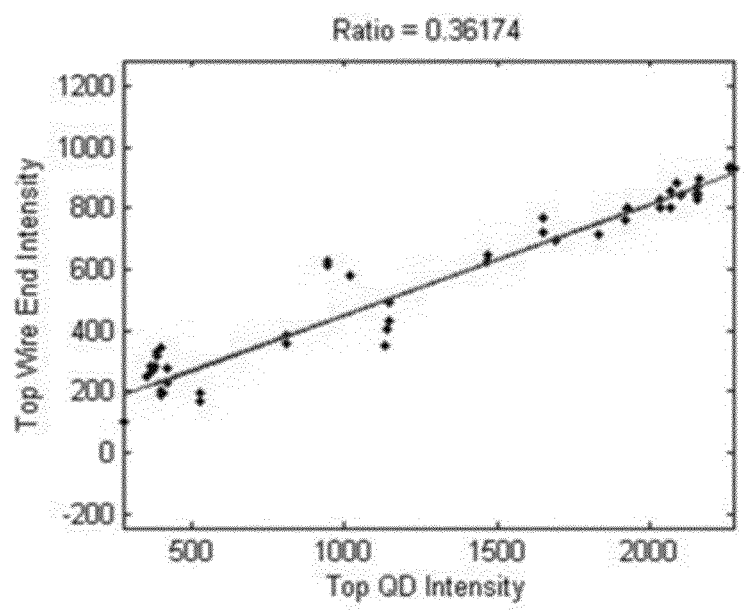
FIGS. 13A-13D are graphs showing the correlation of QD blinking and AgNW end emission. Plots of the relative emission intensity for each QD of the system shown in FIG. 12 and each end of the AgNW are shown in FIGS. 13A-13D.
Figure 13B:
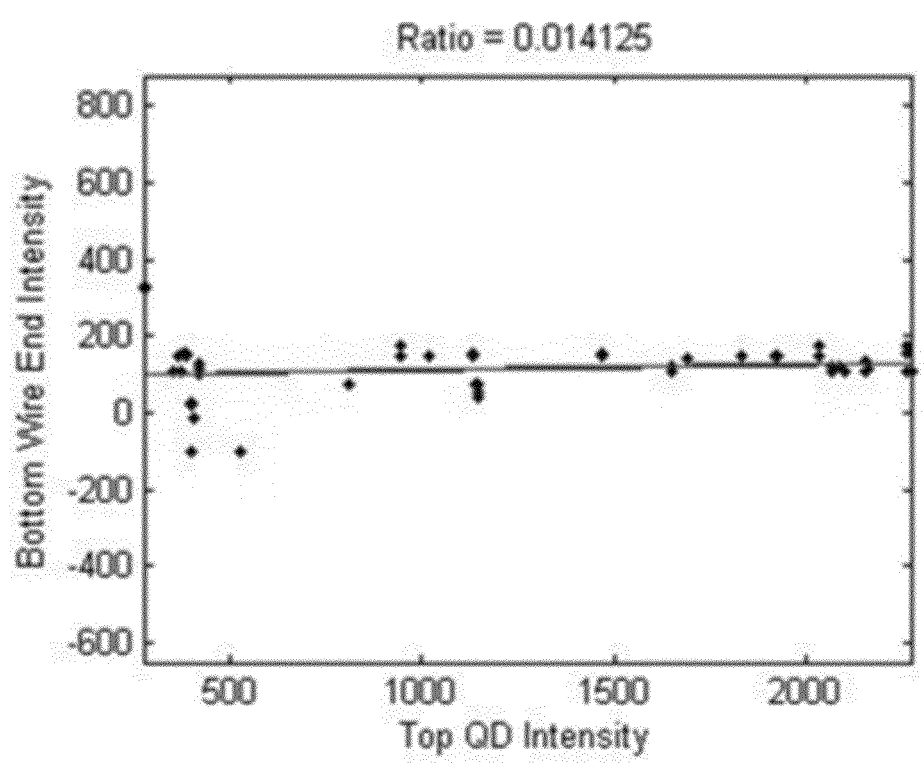
Figure 13C:
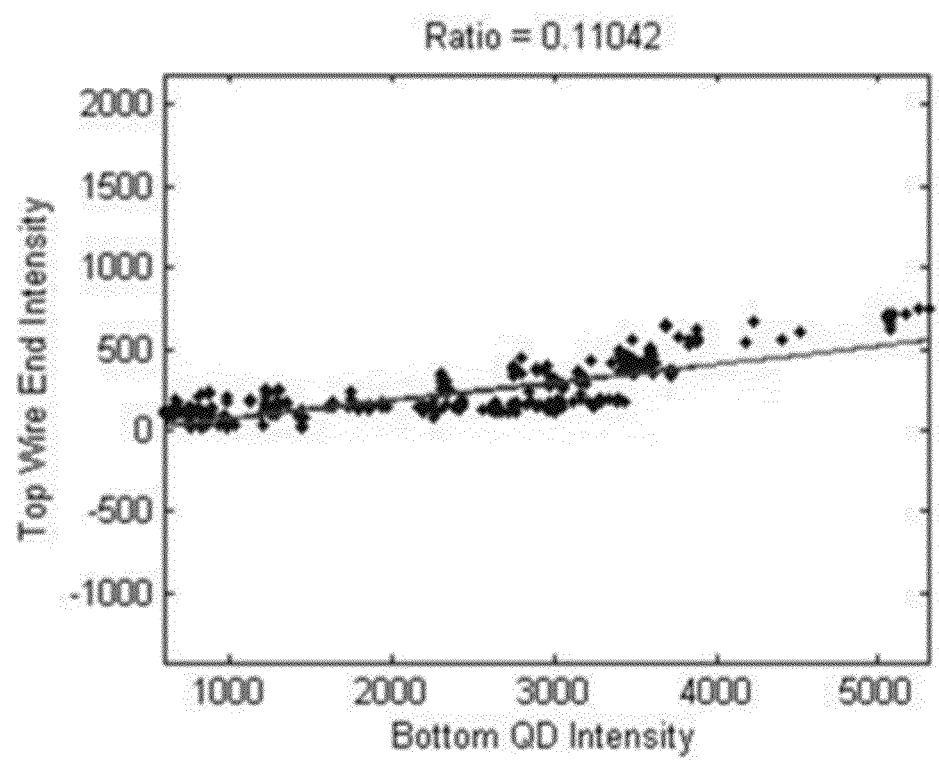
Figure 13D:
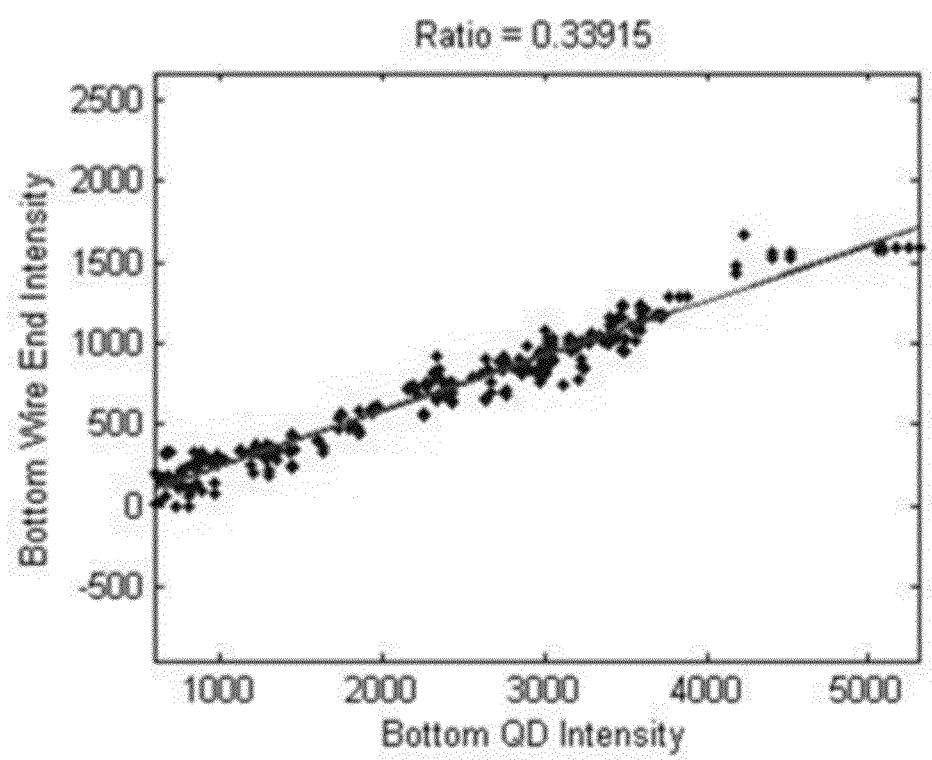

An experiment demonstrating the immobilization of two QDs on an AgNW is shown in FIG. 12. The methods described above may also be used to position and immobilize multiple QDs on a single AgNW. Each time a QD is brought to its desired position on an AgNW, the end of the AgNW is irradiated with ultrafast pulses at 800 to perform immobilization using GMAIL. A representative AgNW that has two QDs attached to it at a distance of 2.5±1 µm is shown in FIG. 12c.

In contrast to the case of the nanowire excitation to a second nanowire, the field enhancement in the case of the nanowire coupling to a QD occurred relatively uniformly along the entire surface of the nanowire, and was not significantly further enhanced in the vicinity of the QD.

Correlation of Blinking of Immobilized QDs with Emission from AgNW Ends

To demonstrate the correlation between the blinking of a QD immobilized on a nanowire and emission from the nanowire ends, video of an AgNW with two immobilized QDs (the system shown in FIG. 12) was analyzed. The two QDs were near opposite ends of the AgNW (FIG. 12c). As shown in FIGS. 13A-D, the emission from each end of the nanowire is strongly correlated with (but less intense than) the emission of the QD closest to it. There is also a correlation between the blinking of a QD and emission from the far end of the AgNW, but in this case the emission from the AgNW is far weaker than the emission from the QD. While in this case we sometimes observe QD emission without observing AgNW emission, we did not observe strong AgNW emission that is stronger than the QD emission.

Concluding Discussion

The efficient generation of MAIL at the end of an AgNW allows the nanowire to act as its own far-field-to-near-field converter. Broadband visible light generated at the excited end of the AgNW can propagate for many micrometers to the distal end, where it is emitted as visible and UV radiation and can drive localized photochemistry. Further, leakage from the waveguide can also lead to localized photochemistry wherever another nanostructure contacts the AgNW.

The disclosed methods demonstrate that nonlinear light/matter interactions allow metal nanowires to act as their own near-field optical couplers. The efficient generation and coupling of broadband visible radiation at one end of a nanowire (e.g., an AgNW) allows localized, nanoscale photochemistry to be driven at the far end of the nanowire or at any location along the length of the nanowire that is in contact with another nanoscale object or structure. By using the disclosed methods in concert with the fluid-based nanomanipulation of individual nanoparticles (see Ropp, C. et al., "Manipulating Quantum Dots to Nanometer Precision by Control of Flow," Nano Lett., 10:2525-2530 (2010)), on-demand, high-precision fabrication of nanophotonic devices based on nanowires is achieved.

GMAIL can be used to drive virtually any photochemical or photophysical process without direct laser irradiation of the region of interest. This capability offers great potential for applications such as biological studies involving localized photouncaging or fluorescence excitation, materials imaging, and photolithography.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of guiding radiation in a nanowire, comprising the steps of:
   providing a nanowire having a first portion and a second portion;
   irradiating solely said first portion of said nanowire with near-infrared radiation, thereby exciting said first portion to generate ultraviolet radiation; and
   guiding the generated ultraviolet radiation from said first portion along said nanowire toward said second portion so that said guided ultraviolet radiation is emitted from said second portion at a location remote from said first portion.

2. The method of claim 1, comprising the further step of providing a nanowire having a polymer coating, wherein said polymer coating is polymerized by said emitted ultraviolet radiation to form a polymerized region extending outwardly from said second portion of said nanowire.

3. The method of claim 1, wherein said nanowire comprises a metal selected from the group consisting of silver, nickel, palladium, platinum, copper, zinc, and cadmium.

4. The method of claim 1, wherein said emitted ultraviolet radiation is utilized to illuminate a structure for a nanoimaging application.

5. The method of claim 1, wherein said emitted ultraviolet radiation is utilized to polymerize a photoresist coating on a surface.

6. The method of claim 1, comprising the further steps of:
   positioning a nanoparticle at a selected position on said nanowire prior to said irradiating step; and
   immobilizing said nanoparticle at said selected position following said irradiating step.

7. The method of claim 6, wherein said nanoparticle is selected from the group consisting of a quantum dot, a dye-infused nanobead, and a biomolecule.

8. The method of claim 6, comprising the further step of positioning and immobilizing more than one nanoparticle at selected positions on said nanowire.

9. The method of claim 6, comprising the step of utilizing electroosmotic flow control during said positioning step for moving said nanoparticle to said selected position.

10. A method of fabricating a nanodevice, comprising the steps of:
    providing a nanowire including a first portion and a second portion, said nanowire having a polymer coating;
    providing a nanostructure proximate to said second portion of said nanowire;
    irradiating solely said first portion of said nanowire with near-infrared radiation, thereby exciting said first portion to generate ultraviolet radiation;
    guiding the generated ultraviolet radiation from said first portion along said nanowire toward said second portion so that a region of said polymer coating on said second portion is polymerized and bonds said nanostructure to said nanowire.

11. The method of claim 10, wherein said region of said polymer coating that is polymerized and bonded to said nanostructure is intermediate opposing ends of said nanowire.

12. The method of claim 10, wherein said nanowire bonded to said nanostructure form a nanodevice having a T-shaped configuration.

13. The method of claim 10, comprising the further steps of:
    positioning a nanoparticle at a selected position on said nanowire prior to said irradiating step; and
    immobilizing said nanoparticle at said selected position following said irradiating step.

14. The method of claim 13, wherein said nanoparticle is selected from the group consisting of a quantum dot, a dye-infused nanobead, and a biomolecule.

* * * * *